United States Patent [19]

Zimmerman

[11] 4,333,760

[45] Jun. 8, 1982

[54] HERBICIDAL SULFONAMIDES

[75] Inventor: William T. Zimmerman, Wilmington, Del.

[73] Assignee: E. I. Du Pont de Nemours and Company, Wilmington, Del.

[21] Appl. No.: 269,510

[22] Filed: Jun. 9, 1981

Related U.S. Application Data

[63] Continuation-in-part of Ser. No. 180,483, Aug. 22, 1980, abandoned.

[51] Int. Cl.³ .................. A01N 43/54; C07D 239/84

[52] U.S. Cl. ........................................ 71/92; 544/284; 544/292

[58] Field of Search ..................... 71/92; 544/284, 292

[56] References Cited

U.S. PATENT DOCUMENTS

| | | | |
|---|---|---|---|
| 4,214,890 | 7/1980 | Levitt | 71/92 |
| 4,238,621 | 12/1980 | Levitt | 71/92 |
| 4,257,802 | 3/1981 | Levitt | 71/93 |

Primary Examiner—Paul M. Coughlan, Jr.

[57] ABSTRACT

Novel arylsulfonylureidoquinazolines are useful as herbicides and plant growth regulants.

21 Claims, No Drawings

HERBICIDAL SULFONAMIDES

This application is a continuation-in-part of my copending application Ser. No. 180,483, filed Aug. 22, 1980, now abandoned.

BACKGROUND OF THE INVENTION

This invention relates to a novel class of arylsulfonylureidoquinazolines and their use as herbicides and plant growth regulants.

Unexamined European Patent No. 7687, teaches arylsulfonylureidopyrimidines such as N-[(4,6-dimethylpyrimidin-2-yl)aminocarbonyl]-2-methoxycarbonylbenzenesulfonamide.

U.S. Pat. No. 4,169,719, issued Oct. 2, 1979 to George Levitt, teaches arylsulfonylureidopyrimidines such as N-[(4,6-dimethylpyrimidin-2-yl)aminocarbonyl]-2-chlorobenzenesulfonamide.

The presence of undesired vegetation causes substantial damage to useful crops, especially agricultural products that safisfy man's basic food and fiber needs such as cotton, rice, corn, wheat and the like. The current population explosion and concomitant world food and fiber shortage demand improvements in producing these crops. Preventing or mimimizing loss of a portion of such valuable crops by killing or inhibiting the growth of undesired vegetation is one way of improving this efficiency.

A wide variety of materials useful for killing or inhibiting (controlling) the growth of undesired vegetation are available; such materials are commonly referred to as herbicides. The need still exists, however, for effective herbicides that destroy or control weeds while not significantly damaging useful crops.

SUMMARY OF THE INVENTION

According to this invention, there are provided novel compounds of Formula I, suitable agricultural compositions containing them and methods of using them as herbicides having both pre-emergence and post-emergence activity and growth regulants:

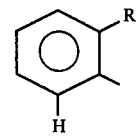

where
A is

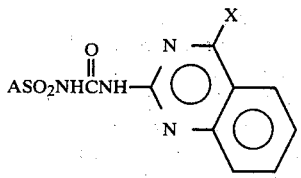

R is $NO_2$, $CF_3$, $COR_3$, $S(O)_mR_4$, $SO_2NR_5R_6$ or $SO_2N(CH_3)(OCH_3)$;
$R_1$ is H, Cl or $CH_3$;
$R_3$ is $C_1$–$C_3$ alkyl, $C_1$–$C_3$ alkoxy, $OCH_2CH=CH_2$, $OCH_2CH_2Cl$, $OCH_2CH_2OCH_3$, $NR_7R_8$ or $C_1$–$C_3$ alkylthio;
m is 0, 1 or 2;

$R_4$ is $C_1$–$C_3$ alkyl;
$R_5$ and $R_6$ are independently $C_1$–$C_2$ alkyl;
$R_7$ is $C_1$–$C_2$ alkyl or $OCH_3$;
$R_8$ is $C_1$–$C_2$ alkyl or $R_7$ and $R_8$ can be taken together to form

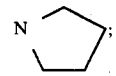

$R_2$ is Cl or $SO_2R_9$;
$R_9$ is $C_1$–$C_3$ alkyl; and
X is H or $CH_3$; and their agriculturally suitable salts; provided that when $R_7$ is $OCH_3$ then $R_8$ is $CH_3$.

Preferred in increasing order for reasons of higher herbicidal activity and/or lower cost and/or ease of synthesis are:

(1) those compounds of the generic scope in which X is $CH_3$;
(2) compounds of Preferred 1 in which $R_1$ is H;
(3) compounds of Preferred 2 in which A is

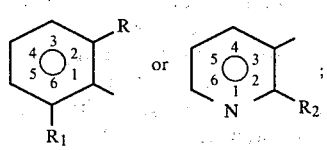

(4) compounds of Preferred 3 in which
R is $NO_2$, $SO_2NR_5R_6$, or $COR_3$ and
$R_3$ is $C_1$–$C_3$ alkoxy.

Specifically preferred for reasons of highest activity and/or lowest cost and/or greatest ease of synthesis are:
N-[(4-methylquinazolin-2-yl)aminocarbonyl]-2-nitrobenzenesulfonamide; and
methyl 2-[[(4-methylquinazolin-2-yl)aminocarbonyl]aminosulfonyl]benzoate.

Synthesis

As shown in Equation 1, the compounds of Formula I can be prepared by combining an appropriate 2-aminoquinazoline of Formula II with an appropriately substituted sulfonylisocyanate of Formula III; A and X being as previously defined, provided $R_3$ is not alkyl, dialkylamino, or alkylthio, and m is not 1.

Equation 1

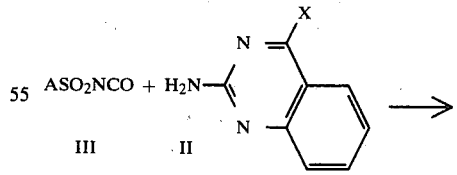

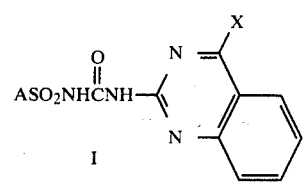

The reaction is best carried out in inert aprotic organic solvents such as methylene chloride, tetrahydrofuran or acetonitrile, at ambient pressure and temperature. The mode of addition is not critical; however, it is often convenient to add the sulfonyl isocyanate to a stirred suspension of the aminoquinazoline. Since such isocyanates usually are liquids, their addition can be easily controlled.

The reaction is generally exothermic. In some cases, the desired product is insoluble in the warm reaction medium and crystallizes from it in pure form. Products soluble in the reaction medium are isolated by evaporation of the solvent, trituration of the solid residue with solvents such as 1-chlorobutane or ethyl ether, and filtration.

a. Sulfonyl Isocyanate Intermediates

The intermediate aryl sulfonyl isocyanate of Formula II can be prepared by reacting corresponding aryl sulfonamides with phosgene in the presence of n-butyl isocyanate at reflux in a solvent such as chlorobenzene, according to the procedure of H. Ulrich and A. A. Y. Sayigh, *New Methods of Preparative Organic Chemistry*, Vol. VI, p. 223–241, Academic Press, New York and London, W. Foerst Ed. The intermediate pyridyl sulfonyl isocyanate of Formula II can be prepared by reacting an N-(alkylaminocarbonyl)pyridinesulfonamide with phosgene as described in unexamined European Pat. No. 13,480, the disclosure of which is hereby incorporated by reference. The N-(alkylaminocarbonyl)-pyridinesulfonamide can be prepared, as described in unexamined European Pat. No. 13,480, by the reaction of a pyridinesulfonamide, an alkyl isocyanate and an anhydrous base in an anhydrous solvent.

The preparation of sulfonamides from ammonium hydroxide and sulfonyl chloride is widely reported in the literature, e.g., Crossley et al., *J. Am. Chem. Soc.* 60, 2223 (1938). The preparation of pyridylsulfonamide is described in G. Machek, *Monatsch* 2, 84 (1939) and L. Thunus and C. L. Lapiere, *Ann. Farn* 33, 663 (1975).

Certain sulfonyl chlorides are best prepared by chlorosulfonation of a substituted benzene in carbon tetrachloride according to the teaching of H. T. Clarke et al., *Org. Synth.* Coll. Vol. 1, 2nd Ed., 1941, p. 85. Other benzenesulfonyl chlorides are best made by diazotization of the appropriate aniline with sodium nitrite in HCl, followed by reaction of the diazonium salt with sulfur dioxide and cuprous chloride in acetic acid according to the teaching of H. L. Yale and F. Sowinski, *J. Org. Chem.* 25, 1824 (1960). The preparation of pyridyl sulfonyl chlorides is described in *Chem. Abs.* 88, 190603 m (1978).

A different method is used for preparing the intermediate sulfonyl isocyanate of Formula II when the intermediate is an o-sulfamoylbenzenesulfonyl isocyanate. This method is illustrated by Equations 2a–e.

Equations 2a–e

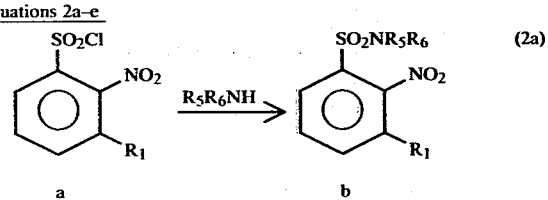

a       b

Equations 2a–e

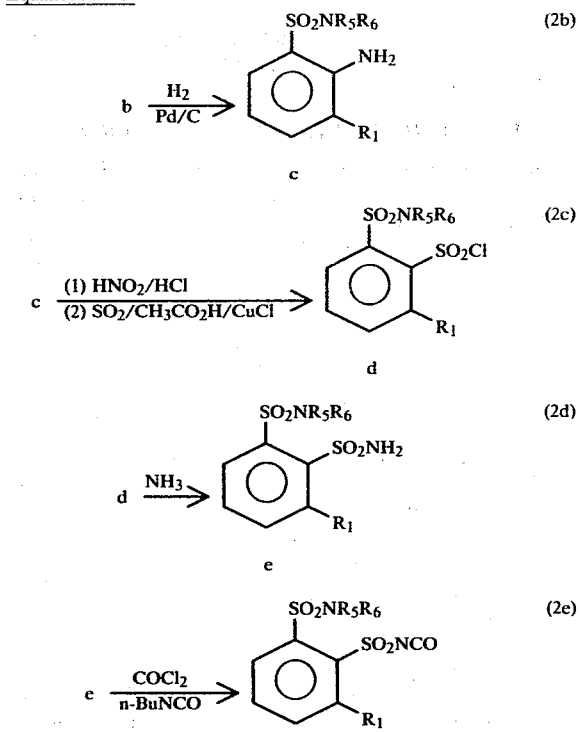

wherein
$R_1$, $R_5$ and $R_6$ are as defined previously.

In step (2a), the o-nitrobenzenesulfonyl chlorides in Formula a, which are well-known in the art, are treated with an amine, $R_5R_6NH$, in an inert organic solvent such as methylene chloride, ethyl ether, or tetrahydrofuran at 0°–50°. The amine may be taken in excess to act as an acid acceptor; alternatively, a tertiary amine such as triethylamine or pyridine may be used as an acid acceptor. The by-product amine hydrochloride is filtered off or washed out of the solvent with water and the product isolated by evaporation of the solvent.

The reduction described in step (2b) is accomplished by treating a solution of the compounds of Formula b in a solvent such as ethanol, ethyl acetate, or DMF, in a pressure vessel with 100–1000 pounds per square inch of hydrogen at 80°–150° in the presence of a hydrogenation catalyst such as 5–10% palladium absorbed on carbon. When the theoretical amount of hydrogen has been absorbed, the solution is cooled and the catalyst is removed by filtration. The product is then isolated by evaporation of the solvent.

The diazotization and coupling with sulfur dioxide, described in step (2c), is accomplished in the following manner. A solution of the o-sulfamoyl aniline of Formula c in a mixture of concentrated hydrochloric acid and glacial acetic acid is treated with a solution of sodium nitrite in water at −5 to 0°. After stirring for 10–15 minutes at 0° to insure complete diazotization, this solution is added to a mixture of an excess of sulfur dioxide and a catalytic amount of cuprous chloride in glacial acetic acid at 0°–5°. The temperature is kept at 0°–5° for ¼ to 1 hour and is then raised to 20°–25° and held at that temperature for 2–4 hours. This solution is then poured into a large excess of ice water. The sulfonyl chloride products, d, can be isolated by filtration or by extraction into solvent such as ethyl ether or methylene chloride followed by evaporation of the solvent.

The amination described in step (2d) is conveniently carried out by treating a solution of the sulfonyl chloride in Formula d with an excess of anhydrous ammonia in a solvent such as ethyl ether or methylene chloride at 0°–25°. If the product sulfonamide is insoluble it may be isolated by filtration followed by washing out the salts with water. If the product sulfonamide is soluble in the reaction solution, it may be isolated by filtering off the precipitated ammonium chloride and evaporating the solvent.

Sulfonyl isocyanates of Formula III in which R is $SO_2N(CH_3)OCH_3$ can be prepared by a sequence analogous to that shown in Equations 2a–e.

b. Aminoquinazoline Intermediates

The synthesis of aminoquinazolines of Formula II can be accomplished by the procedures taught by Armarego in "The Chemistry of Heterocyclic Compounds", Interscience Publ., New York and London, Vol. 24, "Quinazolines", pp. 322–390.

c. Special Situations

When $R_3$ is $NR_7R_8$ in Formula I, the compounds of this invention can be prepared by reacting the appropriate compound of Formula IV, with the appropriate alkylaminodialkylaluminum derivative of Formula V. This is illustrated in Equation 3, wherein $Y = 1$ to 3.

Equation 3

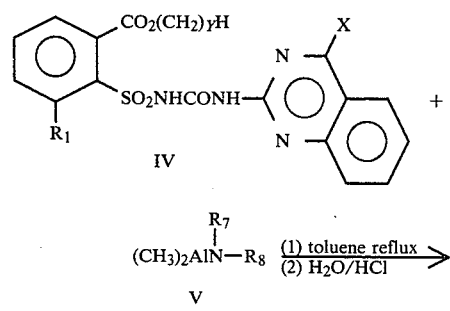

The compounds of Formula IV are prepared in the manner described above. The intermediate alkylaminodialkylaluminum derivatives of Formula V, which are prepared according to A. Basha, M. Lipton and S. Weinreb, *Tetrahedron Letters*, 4171 (1977), are treated with suspensions of the appropriate esters in toluene or a similar inert solvent, and the mixture is refluxed for one to six hours. The product can be isolated by evaporation of the toluene, adding methylene chloride, water and hydrochloric acid to decompose the residual reaction mass and extracting the product into methylene chloride. Evaporation of the methylene chloride yields the desired product, sufficiently pure for the purposes of this invention.

When $R_3$ is $C_1-C_3$ alkylthio, these compounds can be prepared from the esters of this invention wherein $R_3$ is $C_1-C_3$ alkoxy by the reaction of the esters with the appropriate dialkylaluminum alkylthiolate according to Equation 4.

Equation 4

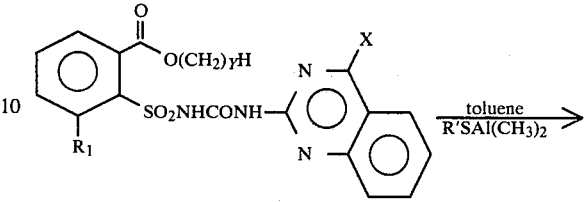

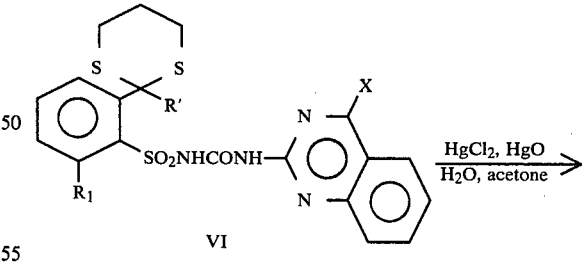

The intermediate aluminum thiolates can be prepared according to R. P. Hatch and S. W. Weinreb, *Journal of Organic Chemistry*, Vol. 42, 3960 (1977). The reaction of the thiolate with the ester of this invention is best carried out in a neutral solvent such as toluene or xylene at reflux for one to three hours. Best results are obtained when the aluminum thiolate compound is present in excess of the stoichiometric amount required.

When $R_3 = C_1-C_3$ alkyl in Formula I, the compounds of this invention can be prepared by reacting a dithiane of Formula VI with mercury salts in aqueous acetone according to the procedures reviewed by D. S. Tarbell and D. P. Harnish, *Chem. Rev.* 49, 67 (1950). This reaction is illustrated in Equation 5 where $R' = C_1-C_3$ alkyl.

Equation 5

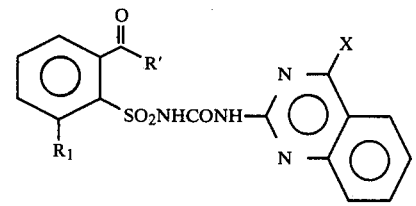

Dithianes of Formula VI can be prepared as outlined in the series of reactions in Equation 6, where $R' = C_1-C_3$ alkyl.

Equation 6a-e

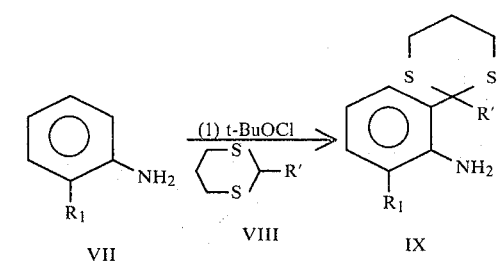 (6a)

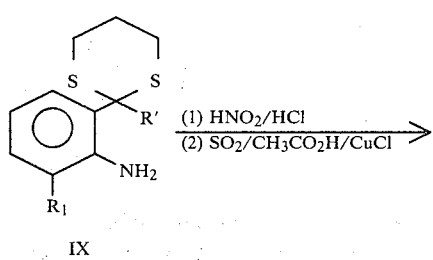 (6b)

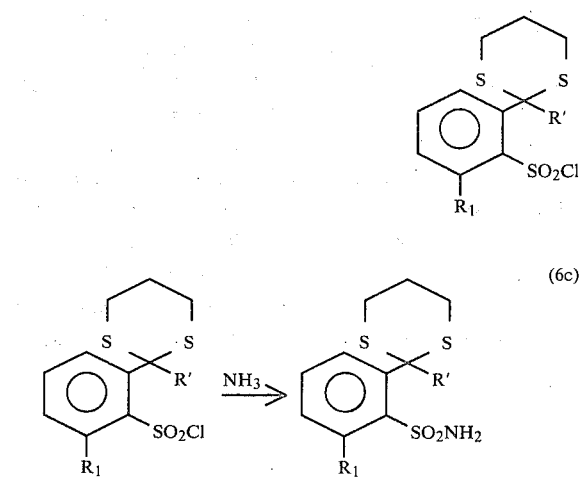

(6c)

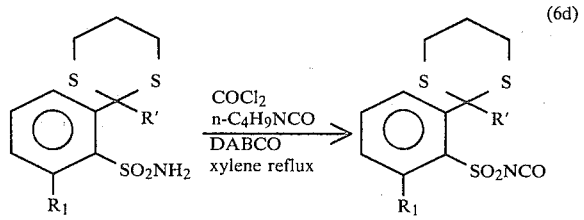 (6d)

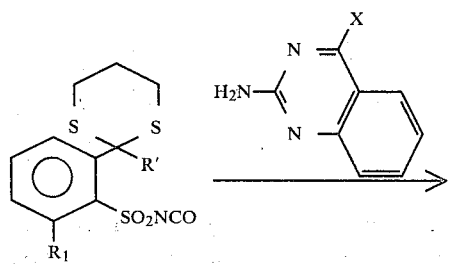 (6e)

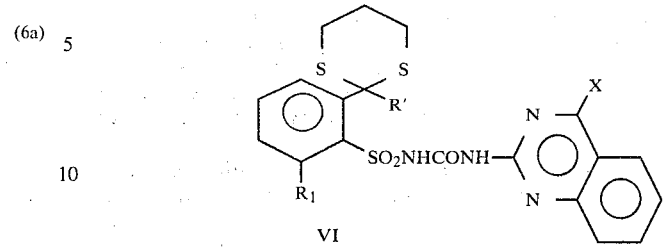

To carry out the reaction in Equation 6a, the aniline VII is treated sequentially in 3:1 acetonitrile-methylene chloride, at $-40°$ C. with tert-butylhypochlorite, the dithiane VIII, and sodium methoxide to provide the o-substituted aniline IX, according to the procedures of P. G. Gassman and H. R. Drewes, *J. Am. Chem. Soc.*, 96, 3002 (1974). The required dithianes VIII are readily available from the corresponding aldehydes or by alkylation of 1,3-dithiane as described by D. Seebach and E. J. Corey, *J. Org. Chem.*, 40, 231 (1975). Conversion of aniline IX to sulfonylurea VI can be accomplished as outlined above.

An alternate method of synthesis of compounds of Formula I ($R_3=C_1-C_3$ alkyl) consists of the reaction of compounds of Formula I ($R_3=OH$) with an excess of organolithium reagent.

Equation 7

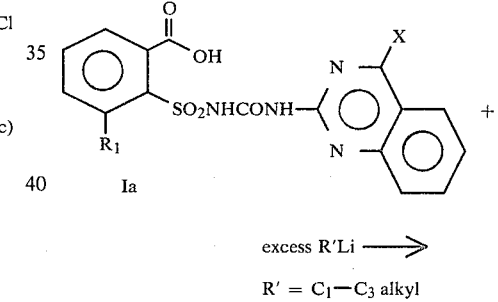

excess R'Li ⟶

R' = $C_1-C_3$ alkyl

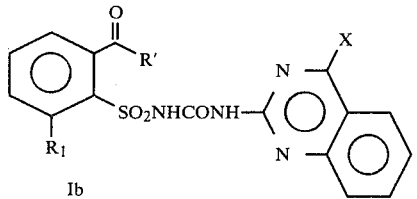

An excess of organolithium compound in a suitable solvent such as diethyl ether, hexane, pentane, or benzene is added to a solution or slurry of Ia in a similar solvent at temperatures between $-100°$ and $0°$ C. The mixture is allowed to warm to room temperature and stir for 30 minutes. Aqueous acid is then added and the compound Ib is extracted into a suitable solvent to free it from salts followed by evaporation of the solvent. Purification is done by chromatography on silica gel.

The synthesis of a wide variety of organolithium compounds by many different procedures is known in the art. A summary of methods with bibliography is contained in *Organo-Metallic Compounds*, G. E. Coates, John Wiley and Sons, 1960, p. 3–21.

Compounds of structure Ia are obtained by hydrolysis of the corresponding methyl ester as shown in Equation 8.

Equation 8

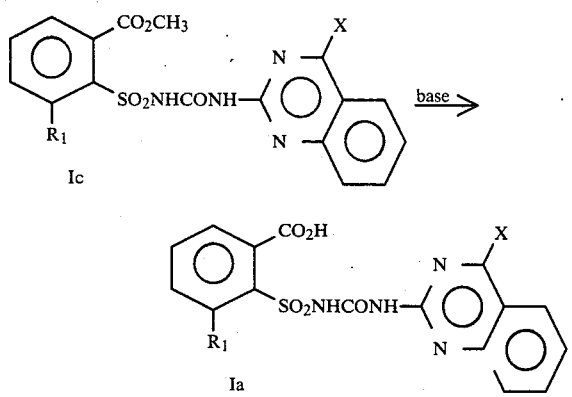

Dissolution of compound Ic in an aqueous methanol or ethanol solution containing KOH, followed by stirring at 0°–25° C. for 6–24 hours yields the soluble potassium salt of the carboxylic acid. The salt is converted to the acid form by addition of strong mineral acids, causing the carboxylic acid Ia to precipitate.

In the cases where $R=S(O)_mR_4$ and $m=1$ in compounds of Formula I, the synthesis is achieved starting from the corresponding thioethers of Formula Ie ($m=0$) as shown in Equation 9, where $R_1$, $R_4$ and X are as defined above.

Equation 9

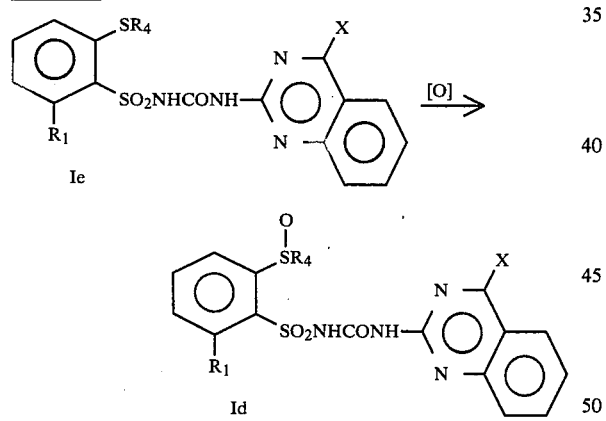

Thioethers of Formula Ie may be oxidized to the corresponding sulfoxides of Formula Id using a wide variety of oxidizing agents known in the art. For example, a methylene chloride solution of Ie is contacted with one equivalent of m-chloroperoxybenzoic acid and the reaction mixture is stirred at ambient temperature for several hours. The resultant suspension is then filtered to remove m-chlorobenzoic acid and the filtrate is evaporated to yield the sulfoxide Id. Other oxidants such as peracetic acid are also conveniently used.

The disclosures of all references cited above are herein incorporated by reference.

Agriculturally suitable salts of compounds of Formula I are also useful herbicides and can be prepared by a number of ways known to the art. For example, metal salts can be made by treating compounds of Formula I with a solution of alkali or alkaline earth metal salt having a sufficiently basic anion (e.g., hydroxide, alkoxide, carbonate or hydride). Quaternary amine salts can be made by similar techniques.

Salts of compounds of Formula I can also be prepared by exchange of one cation for another. Cationic exchange can be effected by direct treatment of an aqueous solution of a salt of a compound of Formula I (e.g., alkali metal or quaternary amine salt) with a solution containing the cation to be exchanged. This method is most effective when the desired salt containing the exchanged cation is insoluble in water, e.g., a copper salt, and can be separated by filtration.

Exchange may also be effected by passing an aqueous solution of a salt of a compound of Formula I through a column packed with a cation exchange resin containing the cation to be exchanged. In this method, the cation of the resin is exchanged for that of the original salt and the desired product is eluted from the column. This method is particularly useful when the desired salt is water soluble, e.g., a potassium, sodium or calcium salt.

Acid addition salts, useful in this invention, can be obtained by reacting a compound of Formula I with a suitable acid, e.g, p-toluenesulfonic acid, trichloroacetic acid or the like.

The compounds of this invention and their preparation are further illustrated by the following examples wherein temperatures are given in degrees Celsius and parts are by weight unless otherwise indicated.

EXAMPLE 1

2-[[(4-methylquinazolin-2-yl)aminocarbonyl]aminosulfonyl]benzoic acid, methyl ester To 20 ml dry acetonitrile was added 1.0 g of 2-amino-4-methylquinazoline followed by 3.1 g of 2-carbomethoxybenzenesulfonyl isocyanate. The slurry was refluxed for 2 hours and allowed to stand at ambient temperature for 16 hours. The light yellow solid was filtered, washed with acetonitrile and dried to yield 1.04 g of methyl 2-[[(4-methylquinazolin-2-yl)aminocarbonyl]aminosulfonyl]benzoate, m.p. 182°–183°. The product showed characteristic absorption bands in the infrared spectrum at 1730 and 1700 cm$^{-1}$ and at 2.9, 3.9 and 7.5–8.4 ppms in the nuclear magnetic resonance spectrum (60 MHz), indicating the title compound.

By application of the procedures of Example 1 and using the appropriate reactants, the compounds of Table I can be prepared.

TABLE I

| R | $R_1$ | X | m.p. (°C.) |
|---|---|---|---|
| $NO_2$ | H | $CH_3$ | 180–183° |
| $NO_2$ | $CH_3$ | $CH_3$ | |
| $NO_2$ | Cl | $CH_3$ | |
| $CF_3$ | H | $CH_3$ | |
| $CF_3$ | H | H | |
| $CO_2CH_3$ | H | $CH_3$ | 182–183° |
| $CO_2CH_3$ | H | H | |
| $CO_2CH_3$ | Cl | $CH_3$ | |
| $CO_2CH_2CH_2CH_3$ | H | $CH_3$ | |
| $CO_2CH_2CH=CH_2$ | H | $CH_3$ | |

TABLE I-continued

[Structure: cyclohexane with R, R1, SO2NHCONH- linked to a bicyclic N,N ring system with X substituent]

| R | R₁ | X | m.p. (°C.) |
|---|---|---|---|
| CO₂CH₂CH₂Cl | H | CH₃ | |
| CO₂CH₂CH₂OCH₃ | H | CH₃ | |
| SCH₃ | H | CH₃ | |
| SO₂CH₃ | H | CH₃ | 197–198° |
| SO₂CH(CH₃)₂ | H | CH₃ | |
| S(O)CH₂CH₃ | H | CH₃ | |
| SO₂N(CH₃)₂ | H | CH₃ | |
| SO₂N(CH₃)₂ | Cl | CH₃ | |
| SO₂N(CH₃)(CH₂CH₃) | H | CH₃ | |
| SO₂N(CH₂CH₃)₂ | H | CH₃ | |
| SO₂N(CH₃)(OCH₃) | H | CH₃ | |

EXAMPLE 2

2-Chloro-3-pyridinesulfonylisocyanate

To 125 ml of dry xylene was added with stirring 20.7 g of 2-chloro-N-(butylcarbamoyl)-3-pyridinesulfonamide. This solution was heated to reflux, and phosgene added until no further uptake of this gas was observed. It was then cooled, filtered and the solvent was removed in vacuo to yield 2-chloro-3-pyridinesulfonylisocyanate as an oil bp 108°–110° (0.7 mm Hg). This product showed a sharp absorption peak in the infrared region at 2220 cm⁻¹.

EXAMPLE 3

2-Chloro-N-[(4-methylquinazolin-2-yl)aminocarbonyl]-pyridine-3-sulfonamide

To a dry, stirred solution of 8.0 g of 2-amino-4-methylquinazoline in 200 ml of methylene chloride at ambient temperature and pressure is added 13 g of 2-chloropyridin-3-sulfonylisocyanate. The resulting mixture is stirred at reflux for 2 hours and then concentrated at reduced pressure. The residue is triturated with 1-chlorobutane and filtered to yield the desired solid product.

The compounds in Table II can be prepared as outlined in Examples 2 and 3 and using the appropriate reactants.

TABLE II

[Structure: pyridine with SO₂NHCONH- linked to bicyclic N,N system with X substituent, R₂ on pyridine]

| R₂ | X |
|---|---|
| Cl | CH₃ |
| Cl | H |
| SO₂CH₃ | CH₃ |
| SO₂CH₂CH₂CH₃ | CH₃ |
| SO₂CH(CH₃)₂ | H |
| SO₂CH₃ | H |

EXAMPLE 4

2-Dimethylaminocarbonyl-N-[(4-methylquinazolin-2-yl)aminocarbonyl]benzenesulfonamide To 21.2 ml of 25% trimethylaluminum in hexane (2.36 M) in 100 ml dry methylene chloride is added 2.2 g dimethylamine. The mixture is stirred at ambient temperature until evolution of methane gas ceases and then 20.0 g of methyl 2-[[(4-methylquinazolin-2-yl)aminocarbonyl]aminosulfonyl]benzoate and 200 ml of dry toluene is added. The resulting mixture is heated to distill off the methylene chloride and hexane, after which heating is continued at the reflux temperature of toluene. After 2 hours, the toluene is removed in vacuo, and 200 ml of methylene chloride and 100 ml of 10% hydrochloric acid are added. The phases are separated, and the methylene chloride phase is washed once with water, dried over magnesium sulfate, and filtered, and the methylene chloride distilled to yield the desired compound.

By using the procedure of Example 4 with an equivalent amount of an appropriately substituted benzoic acid ester and alkylaminodialkylaluminum or alkylthiodialkylaluminum, the compounds of Table III can be prepared.

TABLE III

[Structure: benzene ring with C(O)R₃, SO₂NHCONH- linked to bicyclic N,N system with X substituent, R₁ on benzene]

| R₃ | X |
|---|---|
| N(CH₃)₂ | H |
| N(CH₃)₂ | CH₃ |
| N(CH₃)(CH₂CH₃) | CH₃ |
| N(CH₂CH₃)₂ | CH₃ |
| N(OCH₃)(CH₃) | CH₃ |
| N(OCH₃)(CH₃) | H |
| | CH₃ |
| [pyrrolidinyl N] | |
| SCH₃ | H |
| SCH₃ | CH₃ |
| SCH₂CH₂CH₃ | CH₃ |

EXAMPLE 5

N-[(4-Methylquinazolin-2-yl)aminocarbonyl]-2-carboxybenzenesulfonamide

A mixture containing 5 g of methyl 2-[[(4-methylquinazolin-2-yl)aminocarbonyl]aminosulfonyl]benzoate, 20 ml of ethanol, 2.5 ml of water and 2.5 g of potassium hydroxide is stirred at ambient temperature and pressure for 18 hours. The mixture is then diluted with water and 20 ml of concentrted hydrochloric acid added with stirring. The resulting precipitate is filtered, washed with water and dried.

EXAMPLE 6

2-Acetyl-N-[(4-methylquinazolin-2-yl)aminocarbonyl]-benzenesulfonamide

A mixture containing 0.86 g of N-[(4-methylquinazolin-2-yl)aminocarbonyl]-2-carboxybenzenesulfonamide in 50 ml of anhydrous tetrahydrofuran is treated with 40 ml of a 1.4 M solution of methyllithium in ether at 25° under a nitrogen atmosphere. The mixture is stirred for 4 hours at ambient temperature and then poured into 500 ml of water containing 10 ml of concentrated hydrochloric acid. The product can be isolated by extraction into methylene chloride followed by evaporation and if necessary, can be purified by preparative thin layer chromatography and/or recrystallization.

Using the procedure of Examples 5 and 6 and the proper reactants, the compounds in Table IV may be prepared.

TABLE IV

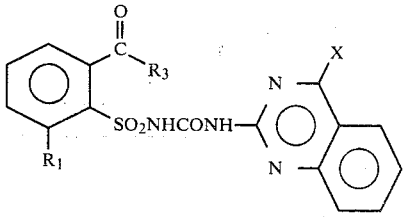

| $R_3$ | $R_1$ | X |
|---|---|---|
| $CH_3$ | H | $CH_3$ |
| $CH_3$ | H | H |
| $CH_3$ | Cl | $CH_3$ |
| $CH_2CH_2CH_3$ | H | $CH_3$ |
| $CH_2CH_2CH_3$ | H | H |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulations, broadly, contain about 0.1% to 99% by weight of active ingredient(s) and at least one of (a) about 0.1% to 20% surfactant(s) and (b) about 1% to 99.9% solid or liquid diluent(s). More specifically, they will contain these ingredients in the following approximate proportions:

TABLE V

| | Active Ingredient | Weight Percent* | |
|---|---|---|---|
| | | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, New Jersey, as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 5th Ed., McGraw-Hill, New York, 1973, pp. 8-57ff.

For further information regarding the art of formulation, see for example:

H. M. Loux, U.S. Pat. No. 3,235,361, Feb. 15, 1966, Col. 6, line 16 through Col. 7, line 19 and Examples 10 through 41;

R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;

H. Gysin and E. Knusli, U.S. Pat. No. 2,891,855, June 23, 1959, Col. 3, line 66 through Col. 5, line 17 and Examples 1–4;

G. C. Klingman, "Weed Control as a Science", John Wiley & Sons, Inc., New York, 1961, pp. 81–96; and J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 7

| Wettable Powder | |
|---|---|
| N-[(4-methylquinazolin-2-yl)aminocarbonyl]-2-nitrobenzene-sulfonamide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 8

| Wettable Powder | |
|---|---|
| Methyl 2-[[(4-methylquinazolin-2-yl)amino-carbonyl]aminosulfonyl]-benzoate | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 9

| Granule | |
|---|---|
| Wettable Powder of Example | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 10

| Extruded Pellet | |
|---|---|
| N-[(4-methylquinazolin-2-yl)aminocarbonyl]-2-nitrobenzenesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 11

| Oil Suspension | |
|---|---|
| Methyl 2-[[(4-methylquinazolin-2-yl)amino-carbonyl]aminosulfonyl]-benzoate | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 12

| Wettable Powder | |
|---|---|
| N-[(4-methylquinazolin-2-yl)amino-carbonyl]-2-nitrobenzenesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

EXAMPLE 13

| Low Strength Granule | |
|---|---|
| N-[(4-methylquinazolin-2-yl)amino-carbonyl]-2-nitrobenzenesulfonamide | 1% |
| N,N-dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 14

| Aqueous Suspension | |
|---|---|
| Methyl 2-[[(4-methylquinazolin-2-yl)amino-carbonyl]aminosulfonyl]-benzoate | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 15

| Solution | |
|---|---|
| N-[(4-methylquinazolin-2-yl)aminocarbonyl]-2-nitrobenzenesulfonamide, sodium salt | 5% |
| water | 95% |

The salt is added directly to the water with stirring to produce the solution, which may then be packaged for use.

EXAMPLE 16

| Low Strength Granule | |
|---|---|
| Methyl 2-[[(4-methylquinazolin-2-yl)amino-carbonyl]aminosulfonyl]-benzoate | 0.1% |
| attapulgite granules | 99.9% |

| -continued |
| --- |
| Low Strength Granule |
| (U.S.S. 20-40 mesh) |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 17

| Granule | |
| --- | --- |
| Methyl 2-[[(4-methylquinazolin-2-yl)amino-carbonyl]aminosulfonyl]-benzoate | 80% |
| wetting agent | 1% |
| crude ligninsulfonate salt (containing 5-20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14-100 mesh (1410-149 microns), and packaged for use.

EXAMPLE 18

| High Strength Concentrate | |
| --- | --- |
| N-[(4-methylquinazolin-2-yl)aminocarbonyl]-2-nitrobenzene-sulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

| Wettable Powder | |
| --- | --- |
| Methyl 2-[[(4-methylquinazolin-2-yl)amino-carbonyl]aminosulfonyl]-benzoate | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 20

| Wettable Powder | |
| --- | --- |
| N-[(4-methylquinazolin-2-yl)amino-carbonyl]-2-nitrobenzene-sulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

| Oil Suspension | |
| --- | --- |
| Methyl 2-[[(4-methylquinazolin-2-yl)amino-carbonyl]aminosulfonyl]-benzoate | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 22

| Dust | |
| --- | --- |
| Methyl 2-[[(4-methylquinazolin-2-yl)amino-carbonyl]aminosulfonyl]-benzoate | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 23

| Emulsifiable Concentrate | |
| --- | --- |
| N-[(4-methylquinazolin-2-yl)amino-carbonyl]-2-nitrobenzene-sulfonamide | 10% |
| blend of oil soluble sulfonates and polyoxyethylene ethers | 4% |
| xylene | 86% |

The ingredients are combined and stirred with gentle warming to speed solution. A fine screen filter is included in packaging operation to insure the absence of any extraneous undissolved material in the product.

The compounds of Formula I can be formulated using the procedures of the above examples.

Utility

The compounds of the present invention are powerful herbicides. They have utility for broad-spectrum pre- and/or post-emergence weed control in areas where complete control of all vegetation is desired, such as around fuel storage tanks, ammunition depots, industrial storage areas, parking lots, drive-in theaters, around billboards, highway and railroad structures. Alternatively, some of the compounds are useful for the selective pre- or post-emergence weed control in crops, such as wheat, corn and sorghum.

The rates of application for the compounds of the invention are determined by a number of factors, including their use as selective or general herbicides, the crop species involved, the types of weeds to be controlled, weather and climate, formulations selected, mode of application, amount of foliage present, etc. In general terms, the subject compounds should be applied at levels of around 0.125 to 10 kg/ha, the lower rates being suggested for use on lighter soils and/or those having a low organic matter content, for selective weed control or for situations where only short-term persistence is required.

The compounds of the invention may be used in combination with any other commercial herbicide examples of which are those of the triazine, triazole, uracil, urea, amide, diphenylether, carbamate and bipyridylium types.

beans with the third trifoliate leaf expanding, crabgrass, barnyardgrass and wild oats with two leaves, cassia with three leaves (including cotyledonary ones), morningglory and cocklebur with four leaves (including the cotyledonary ones), sorghum and corn with four leaves, soybean with two cotyledonary leaves, rice with three leaves, wheat with one leaf, and nutsedge with three-five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. The accompanying descriptive symbols have the following meanings:

G=growth retardation;
C=chlorosis/necrosis;
6Y=abscised buds or flowers;
E=emergence inhibition; and
H=formative effects.

The ratings for the compounds tested by this procedure are presented in Table A. It will be seen that certain of the compounds tested have utility for selective post-emergence weed control in wheat, corn and sorghum.

TABLE A

| kg/ha | 2 | 2/5 | 2 |
|---|---|---|---|
| POST EMERGENCE | | | |
| BUSH BEAN | 8G,5C,6Y | 9G,6C,6Y | 9G,6C,6Y |
| COTTON | 4G,3C,3H | 9G,4C | 9G,6C |
| MORNING GLORY | 3G,1C | 5G,1C | 4G,1C |
| COCKLEBUR | 9G,3C | 6G,1C | 4G,1C |
| CASSIA | 8G,3C | 5G,2C | 2C |
| NUTSEDGE | 9G,1C | 9G | 9G |
| GRABGRASS | 1C | 0 | 3G,1C |
| BARNYARD GRASS | 0 | 8H,3C | 9H,3C |
| WILD OATS | 0 | 0 | 2G,1C |
| WHEAT | 0 | 0 | 3G,1C |
| CORN | 1C | 1C | 8H,1C |
| SOYBEAN | 8G,3C | 8G,1C | 8G,3C |
| RICE | 9G,1C | 9G,4C | 9G,6C |
| SORGHUM | 1C | 9G,1C | 9G,2C |
| PRE EMERGENCE | | | |
| MORNING GLORY | 9G | 9G | 9C |
| COCKLEBUR | 9H | 9G | 9H |
| CASSIA | 8G | 9G,1C | 8G |
| NUTSEDGE | 9G,1C | 9G,1C | 10E |
| CRABGRASS | 1C | 0 | 2C |
| BARNYARD GRASS | 7H,3C | 9H,3C | 9H,3C |
| WILD OATS | 3G,1C | 5G,1C | 6G,1C |
| WHEAT | 7G | 8G | 9H |
| CORN | 8G,1C | 9H | 9G,1C |
| SOYBEAN | 8H | 2G,1C | 6H,2C |
| RICE | 10E | 10E | 10E |
| SORGHUM | 6G,1C | 9H,5C | 10H |

The herbicidal properties of the subject compounds were discovered in a number of greenhouse tests. The test procedures and results follow.

Test A

Seeds of crabgrass (Digitaria spp.), barnyardgrass (Echinochloa crusgalli), wild oats (Avena fatua), Cassia tora, morningglory (Ipomoea spp.), cocklebur (Xanthium spp.), sorghum, corn, soybean, rice, wheat as well as nutsedge tubers were planted in a growth medium and treated pre-emergence with the chemicals dissolved in a non-phytotoxic solvent. At the same time, cotton having five leaves (including cotyledonary ones), bush Test B Two plastic bulb pans were filled with fertilized and limed Fallsington silt loan soil. One pan was planted with corn, sorghum, Kentucky bluegrass and several grassy weeds. The other pan was planted with cotton, soybeans, purple nutsedge (Cyperus rotundus), and several broadleaf weeds. The following grassy and broadleaf weeds were planted: crabgrass (Digitaria sanguinalis), barnyardgrass (Echinochloa crusgalli), wild oats (Avena fatua), johnsongrass (Sorghum halepense), dallisgrass (Paspalum dilatatum), giant foxtail (Setaria fabe-

*rii*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*) and jimsonweed (*Datura stramonium*). A 12.5 cm diameter plastic port was also filled with prepared soil and planted with rice and wheat. Another 12.5 cm pot was planted with sugarbeets. The above four containers were treated pre-emergence.

Twenty-eight days after treatment, the plants were evaluated and visually rated for response to the chemical treatments utilizing the rating system described previously for Test A. The data are summarized in Table B.

TABLE B

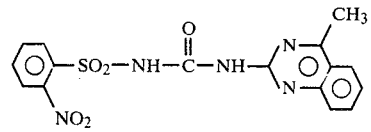

| kg/ha | .0625 | .25 |
|---|---|---|
| PRE EMERGENCE | | |
| CRABGRASS | 0 | 0 |
| BARNYARDGRASS | 0 | 3G |
| SORGHUM | 0 | 5G,3H |
| WILD OATS | 0 | 0 |
| JOHNSONGRASS | 0 | 7G,5H |
| DALLISGRASS | 0 | 3H |
| GIANT FOXTAIL | 0 | 0 |
| KY. BLUEGRASS | 0 | 0 |
| CHEATGRASS | 0 | 0 |
| SUGARBEETS | 0 | 2G |
| CORN | 0 | 0 |
| MUSTARD | 0 | 3G |
| COCKLEBUR | 0 | 0 |
| PIGWEED | 4G | 3G |
| NUTSEDGE | 0 | 0 |
| COTTON | 0 | 0 |
| MORNINGGLORY | 0 | 0 |
| CASSIA | 0 | 0 |
| TEAWEED | 0 | 0 |
| VELVET LEAF | 0 | 0 |
| JIMSONWEED | 0 | 0 |
| SOYBEAN | 0 | 0 |
| RICE | 6G | 6G,3H |

Test C

Twenty-five cm diameter pots filled with Fallsington silt loam were planted to soybeans, cotton, alfalfa, corn, rice, wheat, sorghum, velvetleaf (*Abutilon theophrasti*), sesbania (*Sesbania exaltata*), Cassia (*Cassia tora*), morningglory (*Ipomoea hederacea*), jimsonweed (*Datura stramonium*), cocklebur (*Xanthium pennsylvanicum*), crabgrass (Digitaria spp.), nutsedge (*Cyperus rotundus*), barnyardgrass (*Echinochloa crusgalli*), giant foxtail (*Setaria faberii*) and wild oats (*Avena fatua*). Approximately 2 weeks after planting, the young plants and the soil around them were sprayed overall with the test chemicals dissolved in a non-phytotoxic solvent. Fourteen days after treatment, all species were compared to untreated controls and visually rated for response to treatment. The rating system was as described previously for Test A. The data are presented in Table C.

TABLE C $$\underset{NO_2}{\underset{|}{\bigcirc}}-SO_2-NH-\overset{O}{\underset{\|}{C}}-NH-\underset{N}{\overset{N-\underset{|}{CH_3}}{\bigvee}}\bigcirc$$

| kg/ha | .0625 | .25 |
|---|---|---|
| POST EMERGENCE | | |
| SOYBEANS | 6G,2C | 8G,3C |
| VELVETLEAF | 4G | 7G |
| SESBANIA | 6G,3C | 7G,3C |
| CASSIA | 2C | 3G,3C |
| COTTON | 1C | 4G,3C |
| MORNINGGLORY | 0 | 2C |
| ALFALFA | 0 | 4C |
| JIMSONWEED | 0 | 2C |
| COCKLEBUR | 0 | 0 |
| CORN | 0 | 1C |
| CRABGRASS | 0 | 3G |
| RICE | 0 | 6G |
| NUTSEDGE | 3G | 5G |
| BARNYARDGRASS | 3G,1C | 3G,3C |
| WHEAT | 0 | 0 |
| GIANT FOXTAIL | 0 | 1C |
| WILD OATS | 0 | 2G |
| SORGHUM | 0 | 0 |

$$\bigcirc-SO_2-NH-\overset{O}{\underset{\|}{C}}-NH-\underset{COOCH_3}{\overset{N-\underset{|}{CH_3}}{\bigvee}}\bigcirc$$

| kg/ha | .0625 | .25 |
|---|---|---|
| POST EMERGENCE | | |
| SOYBEANS | 8G,3C | 9G,6C |
| VELVETLEAF | 8G,3C | 9G,1C |
| SESBANIA | 8G,4C | 10G,6C |
| CASSIA | 2C | 3G,2C |
| COTTON | 6G,2C | 9G,5C |
| MORNINGGLORY | 5G | 6G,1C |
| ALFALFA | 5G,2C | 8G,4C |
| JIMSONWEED | — | 0 |
| COCKLEBUR | 2G | 2G |
| CORN | 1G | 3G,2H |
| CRABGRASS | 1C | 2G |
| RICE | 8G,2C | 9G,4C |
| NUTSEDGE | 6G,1C | 7G,2C |
| BARNYARDGRASS | 5G,2C | 6G,4C |
| WHEAT | 0 | 0 |
| GIANT FOXTAIL | 0 | 0 |
| WILD OATS | 0 | 0 |
| SORGHUM | 8G,2C | 9G,1C |

What is claimed is:

1. A compound selected from:

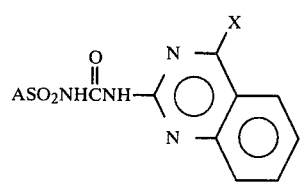

where
A is

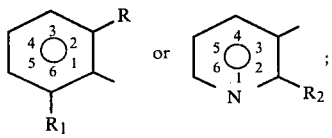

R is $NO_2$, $CF_3$, $COR_3$, $S(O)_mR_4$, $SO_2NR_5R_6$ or $SO_2N(CH_3)(OCH_3)$;
$R_1$ is H, Cl or $CH_3$;
$R_3$ is $C_1$-$C_3$ alkyl, $C_1$-$C_3$ $OCH_2CH=CH_2$, $OCH_2CH_2Cl$, $OCH_2CH_2OCH_3$, $NR_7R_8$ or $C_1$-$C_3$ alkylthio;
m is 0, 1 or 2;
$R_4$ is $C_1$-$C_3$ alkyl;
$R_5$ and $R_6$ are independently $C_1$-$C_2$ alkyl;
$R_7$ is $C_1$-$C_2$ alkyl or $OCH_3$;
$R_8$ is $C_1$-$C_2$ alkyl or
$R_7$ and $R_8$ can be taken together to form

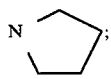

$R_2$ is Cl or $SO_2R_9$;
$R_9$ is $C_1$-$C_3$ alkyl; and
X is H or $CH_3$; and
their agriculturally suitable salts; provided that when $R_7$ is $OCH_3$ then $R_8$ is $CH_3$.

2. A compound of claim 1 in which X is $CH_3$.
3. A compound of claim 2 in which $R_1$ is H.
4. A comound of claim 3 in which A is

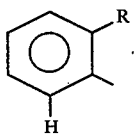

5. A compound of claim 4 in which R is $NO_2$, $SO_2NR_5R_6$, or $COR_3$ and $R_3$ is $C_1$-$C_3$ alkoxy.
6. The compound of claim 1, N-[(4-methylquinazolin-2-yl)aminocarbonyl]-2-nitrobenzenesulfonamide.
7. The compound of claim 1, methyl 2-[[(4-methylquinaolin-2-yl)aminocarbonyl]aminosulfonyl]benzoate.
8. A composition suitable for controlling the growth of undesired vegetation which comprises an effective amount of a compound of claim 1 and at least one of the following: surfactant, solid or liquid diluent.
9. A composition suitable for controlling the growth of undesired vegetation which comprises an effective amount of a compound of claim 2 and at least one of the following: surfactant, solid or liquid diluent.
10. A composition suitable for controlling the growth of undesired vegetation which comprises an effective amount of a compound of claim 3 and at least one of the following: surfactant, solid or liquid diluent.
11. A composition suitable for controlling the growth of undesired vegetation which comprises an effective amount of a compound of claim 4 and at least one of the following: surfactant, solid or liquid diluent.
12. A composition suitable for controlling the growth of undesired vegetation which comprises an effective amount of a compound of claim 5 and at least one of the following: surfactant, solid or liquid diluent.
13. A composition suitable for controlling the growth of undesired vegetation which comprises an effective amount of a compound of claim 6 and at least one of the following: surfactant, solid or liquid diluent.
14. A composition suitable for controlling the growth of undesired vegetation which comprises an effective amount of the compound of claim 7 and at least one of the following: surfactant, solid or liquid diluent.
15. A method for controlling the growth of undesired vegetation which comprises applying to the locus to be protected an effective amount of a compound of claim 1.
16. A method for controlling the growth of undesired vegetation which comprises applying to the locus to be protected an efffective amount of a compound of claim 2.
17. A method for controlling the growth of undesired vegetation which comprises applying to the locus to be protected an effective amount of a compound of claim 3.
18. A method for controlling the growth of undesired vegetation which comprises applying to the locus to be protected an effective amount of a compound of claim 4.
19. A method for controlling the growth of undesired vegetation which comprises applying to the locus to be protected an effective amount of a compound of claim 5.
20. A method for controlling the growth of undesired vegetation which comprises applying to the locus to be protected an effective amount of a compound of claim 6.
21. A method for controlling the growth of undesired vegetation which comprises applying to the locus to be protected an effective amount of the compound of claim 7.

* * * * *